(12) United States Patent
Cantor et al.

(10) Patent No.: US 8,758,298 B2
(45) Date of Patent: *Jun. 24, 2014

(54) LOW-PROFILE MICRONEEDLE ARRAY APPLICATOR

(75) Inventors: Adam S. Cantor, River Falls, WI (US); Franklyn L. Frederickson, White Bear Lake, MN (US); Peter R. Johnson, Eagan, MN (US); Ted K. Ringsred, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,942

(22) Filed: Sep. 12, 2012

(65) Prior Publication Data

US 2013/0006219 A1 Jan. 3, 2013

Related U.S. Application Data

(63) Continuation of application No. 11/718,465, filed as application No. PCT/US2005/041854 on Nov. 18, 2005, now Pat. No. 8,267,889.

(60) Provisional application No. 60/629,215, filed on Nov. 18, 2004.

(51) Int. Cl.
*A61M 5/00* (2006.01)

(52) U.S. Cl.
USPC .......................................... 604/115; 604/117

(58) Field of Classification Search
USPC ................................................. 604/115–117
See application file for complete search history.

(56) References Cited

U.S. PATENT DOCUMENTS

| | | |
|---|---|---|
| 3,034,507 A | 5/1962 | McConnell et al. |
| 3,072,122 A | 1/1963 | Rosenthal |
| 3,123,212 A | 3/1964 | Taylor et al. |
| 3,136,314 A | 6/1964 | Kravitz |
| RE25,637 E | 9/1964 | Kravitz et al. |
| 3,221,740 A | 12/1965 | Rosenthal |
| 3,246,647 A | 4/1966 | Taylor et al. |
| 3,322,121 A | 5/1967 | Banker |
| 3,466,131 A | 9/1969 | Arcudi |
| 3,510,933 A | 5/1970 | Taylor et al. |
| 3,512,520 A | 5/1970 | Cowan |
| 3,596,660 A | 8/1971 | Melone |

(Continued)

FOREIGN PATENT DOCUMENTS

| | | |
|---|---|---|
| AU | 2005200910 82 | 3/2005 |
| EP | 407063 | 1/1991 |

(Continued)

OTHER PUBLICATIONS

ASTM 0256—06a Standard Test Methods for Determining the Izod Pendulum Impact Resistance of Plastics; 20 pgs.

(Continued)

*Primary Examiner* — Rebecca E Eisenberg

(57) ABSTRACT

An applicator used to apply microneedle arrays to a mammal. In particular, an application device for applying a microneedle device to a skin surface comprising a flexible sheet having a raised central area attached to the microneedle device and a supporting member at or near the periphery of the flexible sheet, wherein the flexible sheet is configured such that it will undergo a stepwise motion in the direction orthogonal to the major plane of the sheet.

20 Claims, 10 Drawing Sheets

(56) References Cited

U.S. PATENT DOCUMENTS

| | | |
|---|---|---|
| 3,675,766 A | 7/1972 | Rosenthal |
| 3,678,150 A | 7/1972 | Szumski et al. |
| 3,688,764 A | 9/1972 | Reed et al. |
| 3,905,371 A | 9/1975 | Stickl et al. |
| 3,964,482 A | 6/1976 | Gerstel et al. |
| 4,109,655 A | 8/1978 | Chacornac |
| 4,237,906 A | 12/1980 | Havstad et al. |
| 4,304,241 A | 12/1981 | Brennan |
| 4,360,016 A | 11/1982 | Sarrine |
| 4,453,926 A | 6/1984 | Galy |
| 4,474,751 A | 10/1984 | Haslam et al. |
| 4,503,856 A | 3/1985 | Cornell et al. |
| 4,517,978 A | 5/1985 | Levin et al. |
| 4,637,403 A | 1/1987 | Garcia et al. |
| 4,858,607 A | 8/1989 | Jordan et al. |
| 4,869,249 A | 9/1989 | Crossman et al. |
| 4,920,977 A | 5/1990 | Haynes |
| 4,924,879 A | 5/1990 | O'Brien |
| 5,192,535 A | 3/1993 | Davis et al. |
| 5,250,023 A | 10/1993 | Lee et al. |
| 5,318,584 A | 6/1994 | Lange et al. |
| 5,340,572 A | 8/1994 | Patel et al. |
| 5,366,469 A | 11/1994 | Steg et al. |
| 5,368,047 A | 11/1994 | Suzuki et al. |
| 5,402,798 A | 4/1995 | Swierczek et al. |
| 5,487,726 A | 1/1996 | Rabenau et al. |
| 5,611,806 A | 3/1997 | Jang |
| 5,879,326 A | 3/1999 | Godshall et al. |
| 5,983,136 A | 11/1999 | Kamen |
| 6,050,988 A | 4/2000 | Zuck |
| 6,091,975 A | 7/2000 | Daddona et al. |
| 6,132,755 A | 10/2000 | Eicher et al. |
| 6,219,574 B1 | 4/2001 | Cormier et al. |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,379,324 B1 | 4/2002 | Gartstein et al. |
| 6,440,096 B1 | 8/2002 | Lastovich et al. |
| 6,454,755 B1 | 9/2002 | Godshall |
| 6,503,231 B1 | 1/2003 | Prausnitz et al. |
| 6,532,386 B2 | 3/2003 | Sun et al. |
| 6,537,242 B1 | 3/2003 | Palmer |
| 6,589,202 B1 | 7/2003 | Powell |
| 6,591,124 B2 | 7/2003 | Sherman et al. |
| 6,595,947 B1 | 7/2003 | Mikszta et al. |
| 6,603,998 B1 | 8/2003 | King et al. |
| 6,611,707 B1 | 8/2003 | Prausnitz et al. |
| 6,623,457 B1 | 9/2003 | Rosenberg |
| 6,713,291 B2 | 3/2004 | King et al. |
| 6,743,211 B1 | 6/2004 | Prausnitz et al. |
| 6,780,171 B2 | 8/2004 | Gabel et al. |
| 6,797,276 B1 | 9/2004 | Glenn et al. |
| 6,830,562 B2 | 12/2004 | Mogensen et al. |
| 6,855,131 B2 | 2/2005 | Trautman et al. |
| 6,881,203 B2 | 4/2005 | Delmore et al. |
| 6,881,538 B1 | 4/2005 | Haddad et al. |
| 6,890,319 B1 | 5/2005 | Crocker |
| 6,908,453 B2 | 6/2005 | Fleming et al. |
| 6,931,277 B1 | 8/2005 | Yuzhakov et al. |
| 7,004,928 B2 | 2/2006 | Aceti et al. |
| 7,250,037 B2 | 7/2007 | Shermer et al. |
| 7,419,481 B2 | 9/2008 | Trautman et al. |
| 7,455,654 B2 | 11/2008 | Cormier et al. |
| 7,798,987 B2 | 9/2010 | Trautman et al. |
| 2001/0044606 A1 | 11/2001 | Inkpen et al. |
| 2002/0032415 A1 | 3/2002 | Trautman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0095134 A1 | 7/2002 | Pettis et al. |
| 2002/0111600 A1 | 8/2002 | Cormier et al. |
| 2002/0123675 A1 | 9/2002 | Trautman et al. |
| 2002/0128599 A1 | 9/2002 | Cormier et al. |
| 2002/0138049 A1 | 9/2002 | Allen et al. |
| 2002/0169416 A1 | 11/2002 | Gonnelli et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0193729 A1 | 12/2002 | Cormier et al. |
| 2002/0198509 A1 | 12/2002 | Mikszta et al. |
| 2003/0045837 A1 | 3/2003 | Delmore et al. |
| 2003/0050602 A1 | 3/2003 | Pettis et al. |
| 2003/0083641 A1 | 5/2003 | Angel et al. |
| 2003/0083645 A1 | 5/2003 | Angel et al. |
| 2003/0135158 A1 | 7/2003 | Gonnelli |
| 2003/0135161 A1 | 7/2003 | Fleming et al. |
| 2003/0161869 A1 | 8/2003 | Hatanaka et al. |
| 2003/0181863 A1 | 9/2003 | Ackley et al. |
| 2003/0199811 A1 | 10/2003 | Sage, Jr. et al. |
| 2003/0199812 A1 | 10/2003 | Rosenberg |
| 2003/0208167 A1 | 11/2003 | Prausnitz et al. |
| 2004/0049150 A1 | 3/2004 | Dalton et al. |
| 2004/0077994 A1 | 4/2004 | Lastovich et al. |
| 2004/0138612 A1 | 7/2004 | Shermer et al. |
| 2004/0176732 A1 | 9/2004 | Frazier et al. |
| 2004/0181203 A1 | 9/2004 | Cormier et al. |
| 2005/0025778 A1 | 2/2005 | Cormier et al. |
| 2005/0027242 A1 | 2/2005 | Gabel et al. |
| 2005/0065463 A1 | 3/2005 | Tobinaga et al. |
| 2005/0065466 A1 | 3/2005 | Vedrine |
| 2005/0065472 A1 | 3/2005 | Cindrich et al. |
| 2005/0096586 A1 | 5/2005 | Trautman et al. |
| 2005/0106226 A1 | 5/2005 | Cormier et al. |
| 2005/0137525 A1 | 6/2005 | Wang et al. |
| 2005/0228313 A1 | 10/2005 | Kaler et al. |
| 2005/0261631 A1 | 11/2005 | Clarke et al. |
| 2007/0021716 A1 | 1/2007 | Hansen |
| 2007/0073220 A1 | 3/2007 | Bunce |
| 2007/0161964 A1 | 7/2007 | Yuzhakov |
| 2008/0051699 A1 | 2/2008 | Choi et al. |
| 2008/0088066 A1 | 4/2008 | Ferguson et al. |
| 2008/0114298 A1 | 5/2008 | Cantor et al. |
| 2008/0195035 A1 | 8/2008 | Frederickson et al. |
| 2009/0198189 A1 | 8/2009 | Simons et al. |
| 2010/0222743 A1 | 9/2010 | Frederickson et al. |
| 2012/0109066 A1 | 5/2012 | Chase et al. |

FOREIGN PATENT DOCUMENTS

| | | |
|---|---|---|
| GB | 1080986 | 8/1967 |
| GB | 2064329 | 6/1981 |
| GB | 2221394 | 2/1990 |
| JP | 6-22941 | 2/1994 |
| JP | 2002-504904 | 2/2002 |
| JP | 2003-321350 | 11/2003 |
| JP | 2003-534881 | 11/2003 |
| WO | WO 96/10630 | 4/1996 |
| WO | WO 98/55109 | 12/1998 |
| WO | WO 00/74766 | 12/2000 |
| WO | WO 01/36037 | 5/2001 |
| WO | WO 01/93931 | 12/2001 |
| WO | WO 04/000389 | 12/2003 |
| WO | WO 2004/009172 | 1/2004 |
| WO | WO 2005/051455 | 6/2005 |
| WO | WO 2005/051476 | 6/2005 |
| WO | WO 2005/058393 | 6/2005 |
| WO | WO 2005/065765 | 7/2005 |
| WO | WO 2005/082596 | 9/2005 |
| WO | WO 2005/123173 | 12/2005 |
| WO | WO 2006/055795 | 5/2006 |
| WO | WO 2006/055802 | 5/2006 |
| WO | WO 2007/002521 | 1/2007 |
| WO | WO 2007/002523 | 1/2007 |
| WO | WO 2011/014514 | 2/2011 |

OTHER PUBLICATIONS

ASTM D638—08 Standard Test Method for Tensile Properties of Plastics; 16 pgs.
ASTM D 1238—04c Standard Test Method for Melt Flow Rates of Thermoplastics by Extrusion Plastometer; 14 pgs.
U.S. Appl. No. 60/578,651, filed Jun. 10, 2004, Frederickson et al.

(56) References Cited

OTHER PUBLICATIONS

Daddona Current Opinion in Drug Discovery and Development 1999 2(2);168-171.

Kaushik et al. Anesthesia Analg., 2001, 92, 502-504.

Henry et al. J. Pharm.Sci., 1998, 87,8,922-925.

McAllister et al. (1) Annual Review of Biomedical Engineering, 2000, 2, 289-313.

McAllister et al. (2) Proceed. Int'l. Symp. Control Release of Bioactive Material, 26, (1999), CRS, 192-193.

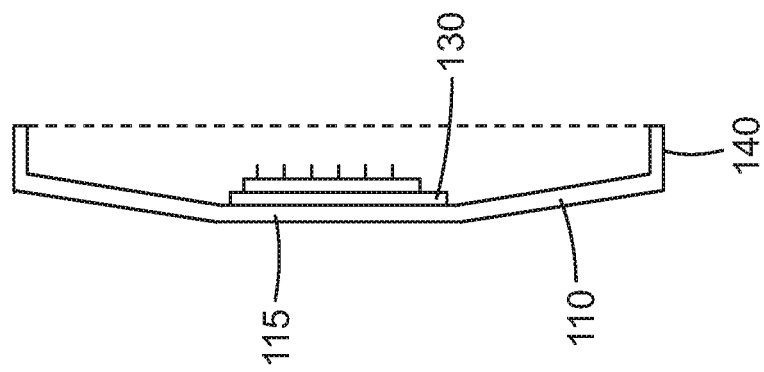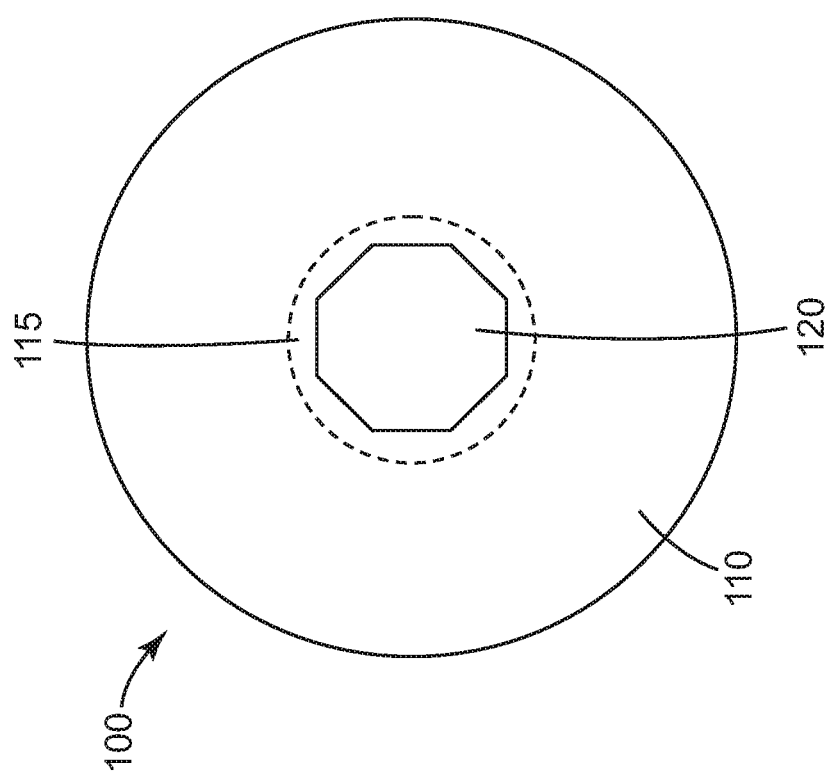

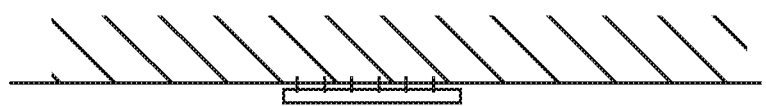
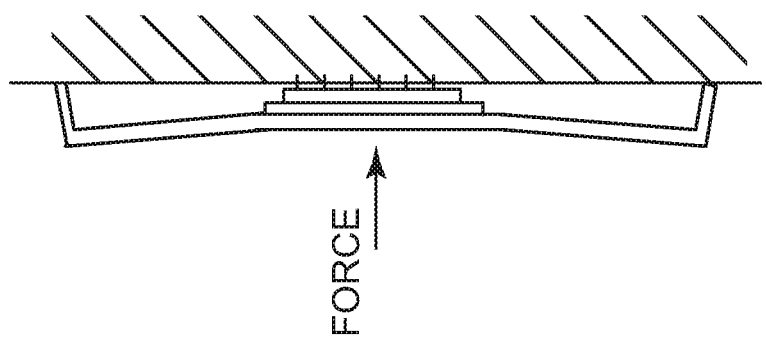
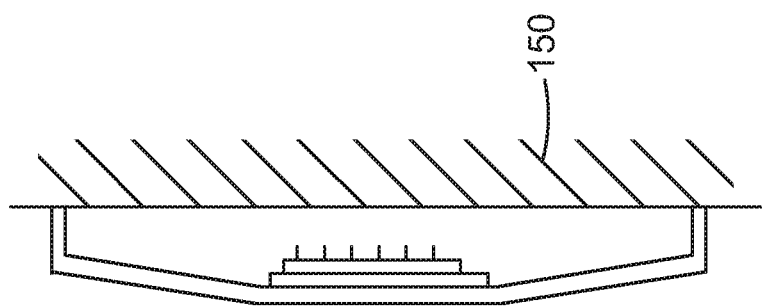

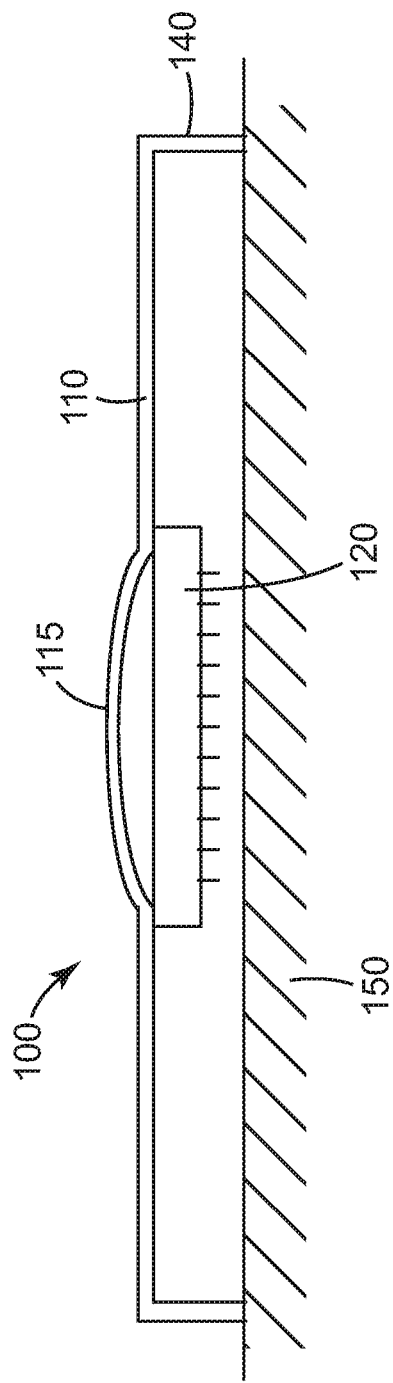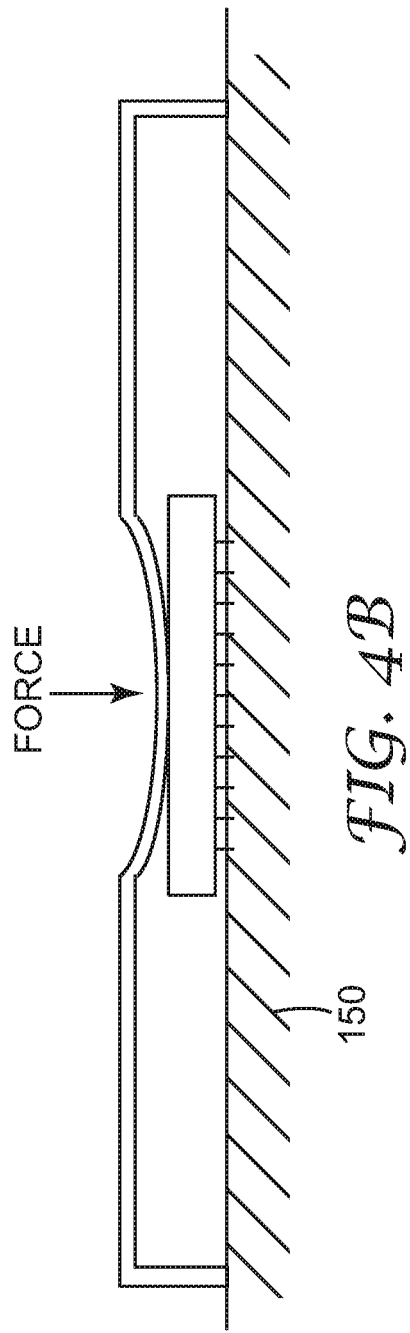

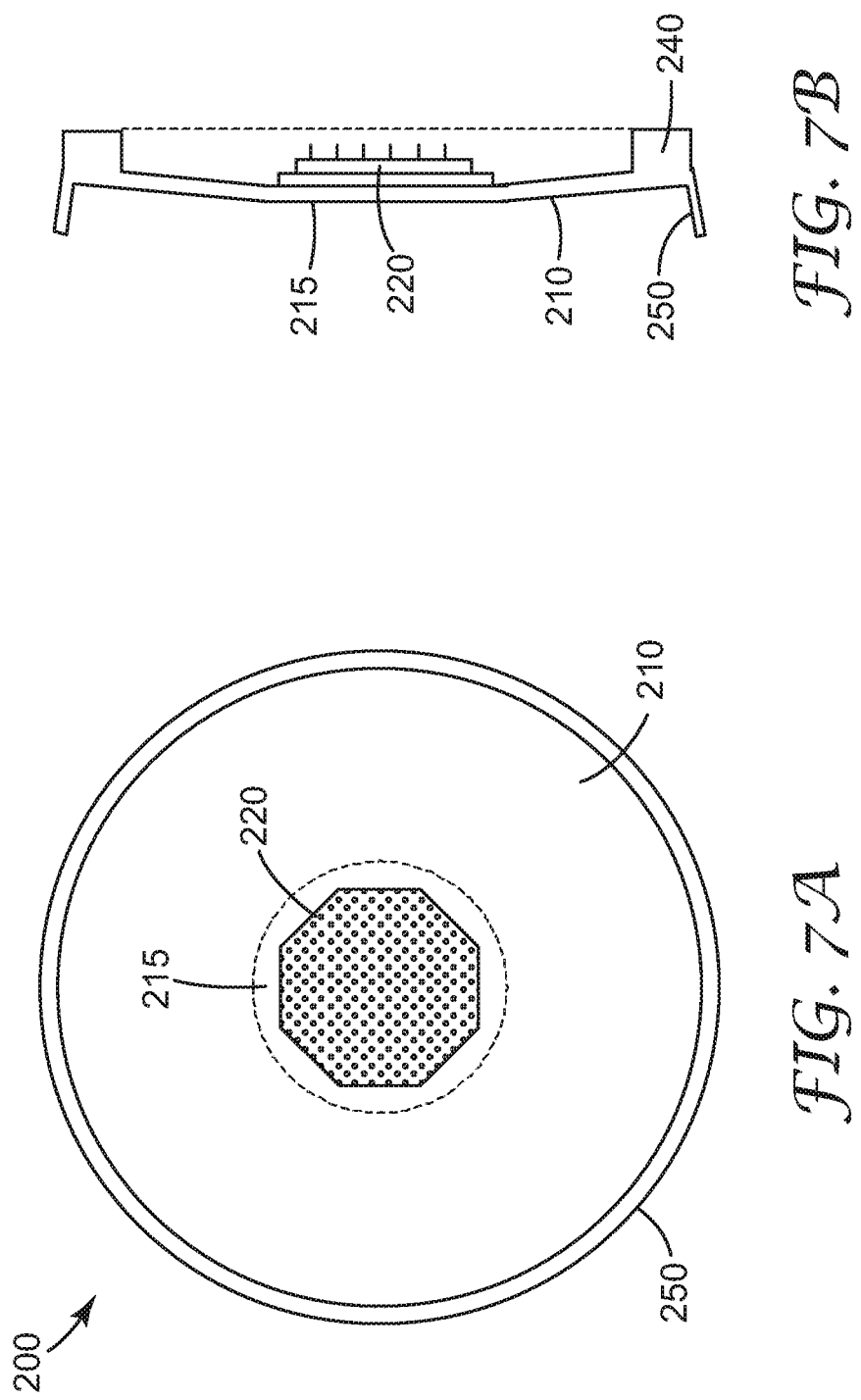

LOW-PROFILE MICRONEEDLE ARRAY APPLICATOR

CROSS-REFERENCE TO RELATED APPLICATIONS

This application is a continuation of U.S. patent application Ser. No. 11/718,465, filed May 2, 2007, now U.S. Pat. No. 8,267,889, which is a national stage filing under 35 U.S.C. 371 of PCT/US2005/041854 filed Nov. 18, 2005, which claims priority to U.S. Provisional Application Ser. No. 60/629,215, filed on Nov. 18, 2004, the disclosure of which is incorporated herein in their entirety.

FIELD

The present invention relates to applicators used to apply microneedle arrays to a mammal. The present method also relates to methods of applying a microneedle array or patch to a mammal

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Issues related to applying microneedles include the ability to effectively insert the needles to a desired depth in the skin and the ability to protect the delicate microneedles prior to application to the skin.

SUMMARY OF THE INVENTION

The present invention provides an application device for applying a microneedle device to a skin surface comprising a flexible sheet having a raised central area wherein motion of the raised central area in a direction perpendicular to the plane of the flexible sheet drives the microneedle device against the skin. This can provide an applicator that is easy to handle, simple to use, low cost, and suitable for inclusion in a disposable device. It can also have a low-profile design.

In another embodiment, the present invention provides an application device for applying a microneedle device to a skin surface comprising: a flexible sheet having a raised central area attached to the microneedle device and a supporting member at or near the periphery of the flexible sheet, wherein the flexible sheet is configured such that it will undergo a stepwise motion in the direction orthogonal to the major plane of the sheet.

In another embodiment, the present invention provides an application device for applying a microneedle device to a skin surface comprising: a flexible sheet having a raised central area configured so as to be releasably attached to a microneedle device and supporting means at or near the periphery of the flexible sheet, wherein the flexible sheet is configured such that it will undergo a stepwise motion in the direction orthogonal to the major plane of the sheet.

In another embodiment, the present invention provides an application device for applying a microneedle device to a skin surface comprising a flexible sheet having a raised central area wherein motion of the raised central area in a direction perpendicular to the plane of the flexible sheet drives the microneedle device against the skin.

In another embodiment, the present invention provides a method of using any one of the foregoing application devices for applying a microneedle array to a skin surface wherein the application device is placed against a skin surface and a force is applied to the device sufficient to cause the flexible sheet of the device to change from a convex to a concave orientation with respect to the skin surface, thereby driving the microneedle array against the skin.

As used herein, certain terms will be understood to have the meaning set forth below:

"Array" refers to the medical devices described herein that include one or more structures capable of piercing the stratum corneum to facilitate the transdermal delivery of therapeutic agents or the sampling of fluids through or to the skin.

"Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein:

FIG. 1A is a schematic plan view of one embodiment of the application device.

FIG. 1B is a schematic cross-sectional view of one embodiment of the application device.

FIG. 2A is a schematic cross-sectional view of one embodiment of the application device placed against a skin surface prior to application of the microneedle device.

FIG. 2B is a schematic cross-sectional view of a microneedle device having been applied to the skin surface.

FIG. 2C is a schematic cross-sectional view of a microneedle device left in place on the skin surface.

FIG. 4A, B is a schematic cross-sectional view of another embodiment of the application device.

FIG. 7A is a schematic plan view of another embodiment of the application device.

FIG. 7B is a schematic cross-sectional view of one embodiment of the application device.

Figure 3:
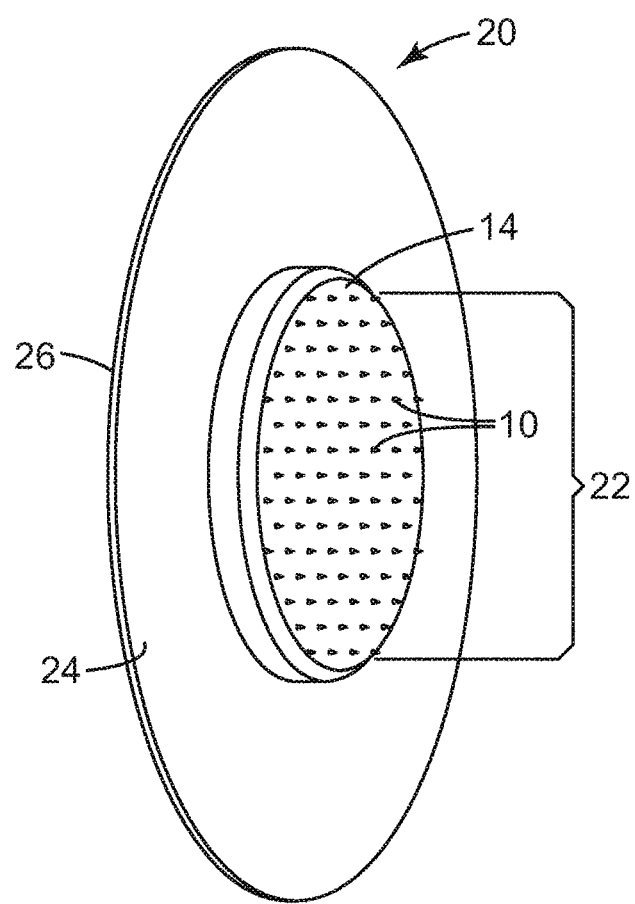
FIG. 3 is a schematic perspective view of patch microneedle device.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers may have been used throughout the figures to denote like parts.

DETAILED DESCRIPTION

One embodiment of the microneedle application device is shown in FIGS. 1A, and 1B. The application device 100 comprises a flexible sheet 110 having a raised central area 115. The sheet comprises a major plane that is oriented generally parallel to a skin surface (as shown in FIG. 2A) during application of a microneedle device 120. The flexible sheet is configured such that it will undergo a stepwise motion in the direction orthogonal to the major plane of the sheet when a sufficient force is applied in the direction orthogonal to the major plane of the sheet (shown in FIG. 2B). This stepwise motion is a sudden movement in the direction of moving the microneedle device 120 towards the skin surface, and is effected by the rapid flexing and inversion of the raised, upwardly bowed central area into a depressed, downwardly bowed central area. This stepwise motion may be associated with a clicking or snapping noise as the flexible sheet moves from a convex orientation (shown in FIG. 2A) to a concave orientation (shown in FIG. 2B). Noise associated with the stepwise motion may be used to indicate to a patient or healthcare provider that the microneedle application device has been triggered and the microneedle device inserted into the skin. It is desirable that a predetermined minimum amount of force is necessary to cause the stepwise motion, thereby resulting in a consistent amount of force being used to apply the microneedle device 120 to the skin surface 150.

The microneedle device 120 may be attached to the flexible sheet 110 by any suitable attachment means. As shown in FIG. 1, the attachment means is an adhesive 130, which may be in the form of a continuous coating, a patterned coating, or discrete portions of adhesive. In one aspect, the adhesive attachment is non-permanent, that is, after application of the microneedle device 120 the flexible sheet 110 may be removed from the skin surface (as shown in FIG. 2C). Alternatively, the flexible sheet may be left in place on the skin surface and serve as a protective backing for the microneedle device. Other suitable attachment means for connecting the microneedle device 120 and the flexible sheet 110 include snap-fit connections, hook and loop (e.g., Velcro™) attachments, magnetic attachment, heat bonding, welding, or any other suitable conventional attachment method known to one of ordinary skill in the art. In one embodiment the microneedle device may be formed or molded as an integral portion of the flexible sheet.

As shown in FIG. 1B, the application device 100 has a supporting member for suspending the microneedle device above the skin surface in the form of a spacer 140, which is a ring around the entire outer edge of the flexible sheet 110 which allows the application device 100 to be placed on the skin (as shown in FIG. 2A) prior to inserting the microneedles into the skin. The spacer 140 may alternatively be in the form of a plurality of legs or any suitable projections (such as those shown in FIGS. 9A, B) that are capable of supporting the flexible sheet in a spaced apart position from the skin surface prior to insertion of the microneedle device. The supporting member should have sufficient rigidity such that it supports or suspends the microneedle device away from the skin until a sufficient force has been applied to the raised central area 115 resulting in the raised central area being depressed.

The microneedle device 120 shown in FIG. 1A has a hexagonal shape, but any of a number of shapes and sizes are suitable for use with application devices of the present invention.

Another embodiment of an application device 100 of the present invention is shown in FIG. 4A-B. In this embodiment the raised central area 115 has a bubble or blister shape that may be depressed as shown. The inherent curvature present in the raised central area may enhance the ability to releasably attach the microneedle device 120 to the flexible sheet 110. As shown, the microneedle device may be attached to the sheet member at attachment points around the periphery of the microneedle device 120 with, for example, an adhesive. Upon insertion into the skin as shown in FIG. 4B, these points of attachment between flexible sheet 110 and microneedle device 120 are separated after insertion of the microneedle device 120 into the skin.

Figure 5B:
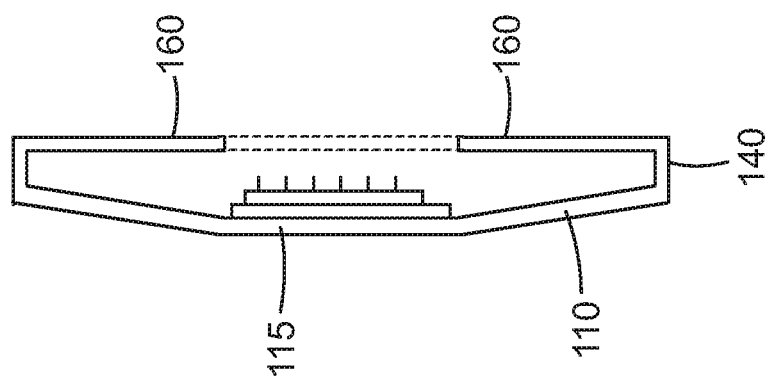
FIG. 5A, B is a schematic plan and cross-sectional view of another embodiment of the application device.
Figure 5A:
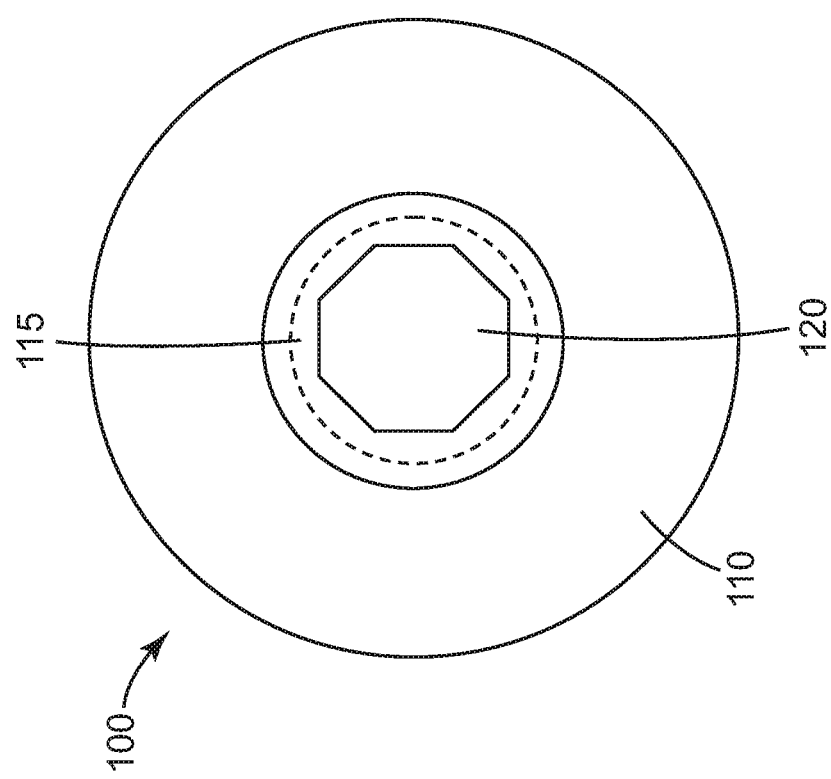
Figure 6A:
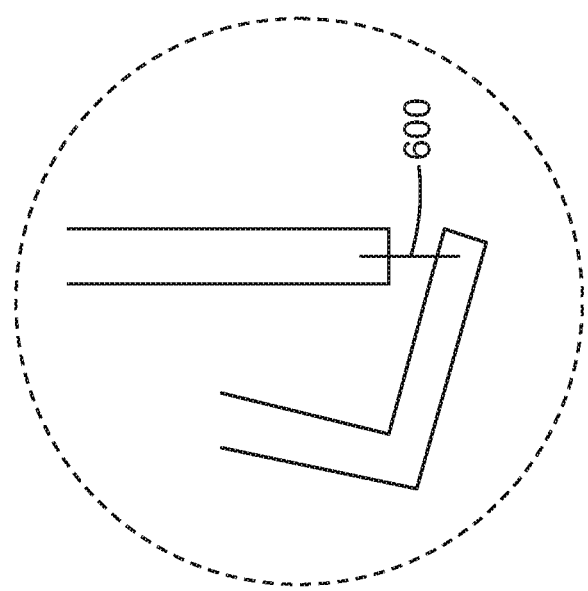
FIG. 6A, B is a schematic view of the application device of FIG. 5A,B in operation.
Figure 6B:
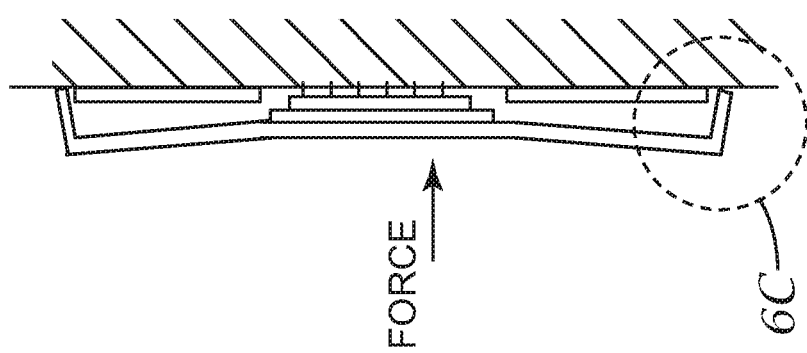
FIG. 6C is an expanded view of the inset portion of FIG. 6B.
Figure 6C:
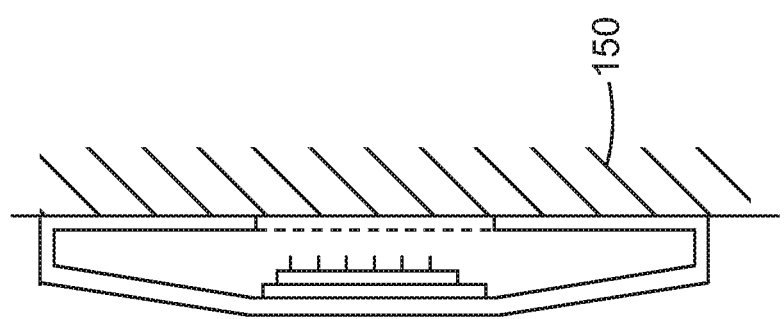

Another embodiment of an application device 100 of the present invention is shown in FIG. 5A-B. This embodiment is similar to that shown in FIG. 1A-B with the addition of a protective face 160 attached to the spacer 140 and designed to be placed against the skin. The protective face 160 may serve to better spread out the force applied to the application device so as to prevent or minimize the spacer pressing uncomfortably into the skin surface during application. The protective face 160 may also serve to keep the skin surface from excessively bowing when pressure is applied onto the raised central area of the application device. The area of the protective face is shown as a shaded area in the FIG. 5A. The opening of the protective face 160 should be sized large enough to allow the microneedle device 120 to easily pass through and contact the skin surface. This embodiment is shown in use in FIGS. 6A, B. As shown, the protective face 160 is integrally formed with the spacer 140 and flexible sheet 110 as a single unit. These may all be formed of individual components connected to each other, as well. It may further be advantageous to have a movable connection 600 between the protective face 160 and the spacer 140 as shown in the expanded view in FIG. 6C. This movable connection may be in the form of a flexible connecting member or a slidable piece holding the two parts together. As shown with an enlarged scale in FIG. 6C, this movable connection allows for free movement of the lower end of the spacer in a direction away from the microneedle device and allows the protective face to remain flat and stationary against the skin surface after application.

Another embodiment of an application device 200 of the present invention is shown in FIGS. 7A-B. The application device 200 comprises a flexible sheet 210 having a raised central area 215. The sheet comprises a major plane that is oriented generally parallel to a skin surface (as shown in FIG. 8A) during application of a microneedle device 220. The flexible sheet 210 has a spacer element 240 that is configured to contact a skin surface during use. The application device 200 also has raised sides 250 attached to the flexible sheet 210 and opposed to the spacer element 240. The flexible sheet is configured such that it will undergo a stepwise motion in the direction orthogonal to the major plane of the sheet when a sufficient force is applied to the raised sides 250 in a direction parallel to the major plane of the sheet (shown in FIG. 8A, B). This stepwise motion is a sudden movement in the direction of moving the microneedle device 220 towards the skin surface, and is effected by the rapid flexing and inversion of the raised, upwardly bowed central area into a depressed, downwardly bowed central area. This stepwise motion may be associated with a clicking or snapping noise as the flexible sheet moves from a convex orientation (shown in FIG. 8A) to a concave orientation (shown in FIG. 8B). Noise associated with the stepwise motion may be used to indicate to a patient or healthcare provider that the microneedle application device has been triggered and the microneedle device inserted into the skin. It is desirable that a predetermined minimum amount of force is necessary to cause the stepwise motion, thereby resulting in a consistent amount of force being used to apply the microneedle device 220 to the skin surface 260.

Flexible sheets of the present invention may be made from any suitable material, including metals, such as aluminum, steel, such as stainless steel, or tin, and plastics, such as polystyrene, polycarbonate, and polypropylene. The flexible sheet with raised central area may be a single, integral piece. Alternatively, the raised central area may be connected to an outer ring, and may be made from the same or from a different material.

A method of applying a microneedle device using an application device of the present invention involves having the microneedle device reach a desired velocity that is effective to pierce the microneedles into the skin. The desired velocity is controlled to limit or prevent stimulation of the underlying nerve tissue. In connection with the present invention, the maximum velocity achieved by the microneedle device upon impact with the skin is often 20 meters per second (m/s) or less, potentially 15 m/s or less, and possibly 10 m/s or less. In some instances, the maximum velocity may be 8 m/s or less. At the lower end of the range of velocities, the minimum velocity achieved by the microneedle device upon impact with the skin is often 2 m/s or more, potentially 4 m/s or more, and possibly 6 m/s or more.

Because of the variability in the location of skin, the application device may be designed such that the microneedle device travels at a velocity at or above the desired minimum velocities over a distance that is sufficient to accommodate the variations in skin location relative to the application device. For example, the microneedle device in the application device may move at or above the minimum desired velocity over a distance of one millimeter or more.

The force required to reach the desired velocities may vary based on the mass and shape of the microneedle application device, and in particular the mass and shape of the flexible sheet and the microneedle device. The mass of the microneedle application device may be controlled or selected to reduce the likelihood that nerve tissue underneath the delivery site is stimulated sufficiently to result in the sensation of pain. For example, it may be preferred that the mass of the microneedle application device be about 6 grams or less, more preferably about 4 grams or less.

In one embodiment, the microneedle device shown schematically as 120 in FIGS. 1 and 2 may be in the form of a patch shown in more detail in FIG. 3. FIG. 3 illustrates a microneedle device comprising a patch 20 in the form of a combination of an array 22, pressure sensitive adhesive 24 and backing 26. A portion of the array 22 is illustrated with microneedles 10 protruding from a microneedle substrate surface 14. The microneedles 10 may be arranged in any desired pattern or distributed over the microneedle substrate surface 14 randomly. As shown, the microneedles 10 are arranged in uniformly spaced rows. In one embodiment, arrays of the present invention have a distal-facing surface area of more than about 0.1 $cm^2$ and less than about 20 $cm^2$, preferably more than about 0.5 $cm^2$ and less than about 5 $cm^2$. As shown, a portion of the substrate surface 16 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 $cm^2$) to less than about 1 square inch (6.5 $cm^2$). In another embodiment (not shown), the microneedles are disposed over substantially the entire surface area of the array 22.

In an alternative embodiment (not shown) the applicator itself includes adhesive on its perimeter, skin-contacting surface, so that the entire applicator can be adhered in place after actuation with the microneedles into the skin for a desired period.

The microneedle devices useful in the various embodiments of the invention may comprise any of a variety of configurations, such as those described in the following patents and patent applications, the disclosures of which are herein incorporated by reference. One embodiment for the microneedle devices comprises the structures disclosed in United States Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in co-pending U.S. patent application Ser. No. 10/621,620 filed on Jul. 17, 2003 which describes microneedles having a truncated tapered shape and a controlled aspect ratio. Still another embodiment for the microneedle devices comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,313,612 (Sherman, et al.) which describes tapered structures having a hollow central channel. Still another embodiment for the micro arrays comprises the structures disclosed in International Publication No. WO 00/74766 (Garstein, et al.) which describes hollow microneedles having at least one longitudinal blade at the top surface of tip of the microneedle.

Microneedle devices suitable for use in the present invention may be used to deliver drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing immune response of vaccine adjuvants. In one aspect, the drug may be applied to the skin (e.g., in the form of a solution that is swabbed on the skin surface or as a cream that is rubbed into the skin surface) prior to applying the microneedle device.

Microneedle devices may be used for immediate delivery, that is where they are applied and immediately removed from the application site, or they may be left in place for an extended time, which may range from a few minutes to as long as 1 week. In one aspect, an extended time of delivery may from 1 to 30 minutes to allow for more complete delivery of a drug than can be obtained upon application and immediate removal. In another aspect, an extended time of delivery may be from 4 hours to 1 week to provide for a sustained release of drug.

EXAMPLES

Example 1

Figure 9A:
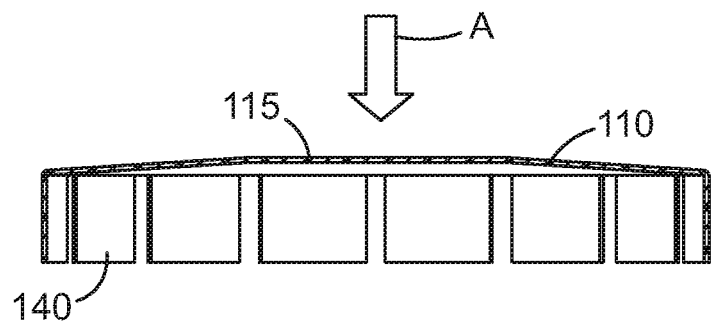
FIG. 9A, B is a schematic plan and side view of another embodiment of the application device.
Figure 9B:
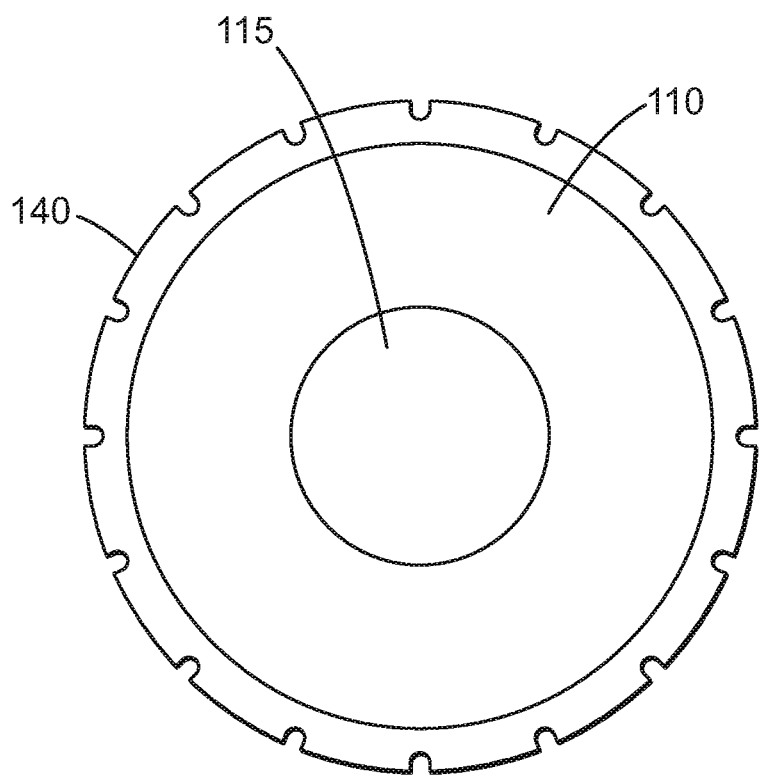
Figure 10:
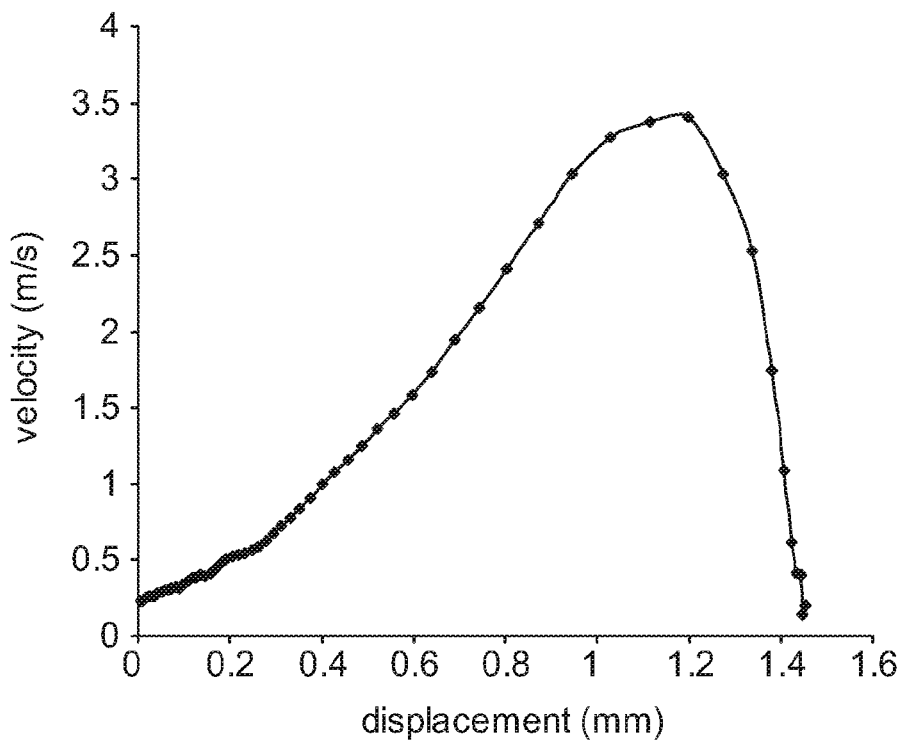
FIG. 10 is a graph of displacement as a function of velocity during use of one embodiment of the application device.

A device as generally shown in FIGS. 9A, B was tested to determine the velocity and displacement with which a microneedle device may be applied. The diameter of the flexible sheet member was approximately 4.5 cm. The diameter of the raised central area was approximately 1.8 cm. The spacer comprised 16 individual fins that were approximately 0.5 cm in height and 0.75 cm in width. The gap between each adjacent fin was approximately 1 mm. A small piece of a matte-finish reflective tape was applied to the underside of the raised central area for purposes of conducting the velocity/displacement measurement, however in practice a microneedle device would be attached to the underside of the raised central area. The flexible sheet member and spacer comprised steel with a thickness of approximately 0.3 mm. The device was placed against a fixture attached to a laser measuring device (Laser Vibrometer Controller model no. OFV-3001 and Laser Fiber Interferometer model no. OFV-502, Polytec Inc., Tustin, Calif.) and aligned such that the laser could reflect off of the matte-finish reflective tape. The raised central area was manually pushed in the direction of the arrow A as shown in FIG. 9A and the resulting velocity as a function of displacement of the raised central area is shown in FIG. 10. Total displacement was approximately 1.45 mm and the maximum velocity recorded was 3.40 m/s. It should be appreciated that the initial displacement of approximately 0.2 mm is due to deformation of the flexible sheet member prior to the stepwise motion induced as the raised central area is inverted. As such, the velocity of the central area during this initial displacement is dependent on the speed that the manual force is applied and may vary from use to use.

Example 2

Figure 8C:
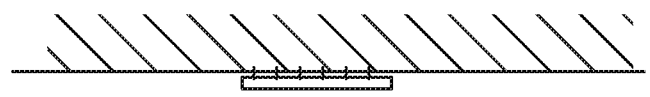
FIG. 8C is a schematic cross-sectional view of a microneedle device left in place on the skin surface.
Figure 8B:
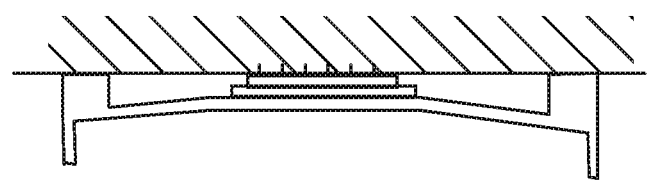
FIG. 8B is a schematic cross-sectional view of the microneedle device of FIG. 8A having been applied to the skin surface.
Figure 8A:
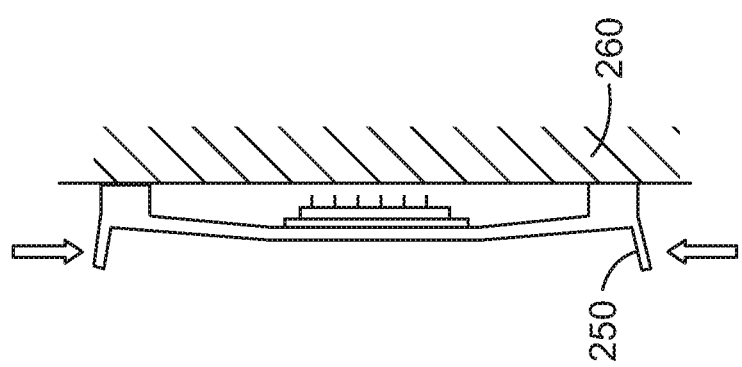
FIG. 8A is a schematic cross-sectional view of the embodiment of the application device shown in FIGS. 7A, B placed against a skin surface prior to application of the microneedle device.
Figure 11:
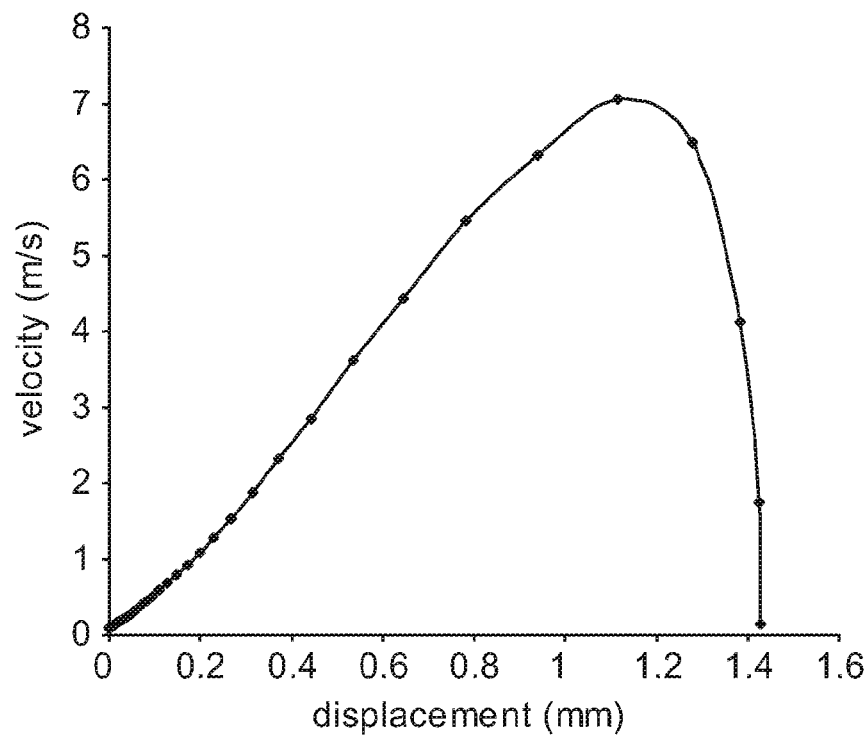
FIG. 11 is a graph of displacement as a function of velocity during use of another embodiment of the application device.

The device of example 1 was tested according to the general mode of operation shown in FIGS. 7 and 8. That is, the raised central area was initially depressed and a small piece of a matte-finish reflective tape was applied to the side of the raised central area opposed to the spacer. The device was placed against a fixture attached to a laser measuring device (Laser Vibrometer Controller model no. OFV-3001 and Laser Fiber Interferometer model no. OFV-502, Polytec Inc., Tustin, Calif.) and aligned such that the laser could reflect off of the matte-finish reflective tape. The spacer was manually pushed in a direction parallel to the plane of the flexible sheet member (as shown in FIG. 8A) and the resulting velocity as a function of displacement of the raised central area is shown in FIG. 11. Total displacement was approximately 1.44 mm and the maximum velocity recorded was 7.06 m/s.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

The invention claimed is:

1. An application device for applying a microneedle device to a skin surface comprising a flexible sheet having a raised central area, a microneedle device attached to the raised central area, a major plane, and a periphery, wherein motion of the raised central area in a direction perpendicular to the major plane of the flexible sheet drives the microneedle device against the skin surface, and wherein the flexible sheet is configured such that it will undergo a stepwise motion in the direction orthogonal to the major plane of the sheet.

2. A device according to claim 1 wherein the stepwise motion moves the raised central area closer to the skin surface.

3. A device according to claim 1 further comprising a supporting member at or near the periphery of the flexible sheet, wherein the supporting member comprises a spacer attached to the periphery of the flexible sheet.

4. A device according to claim 3 further comprising an adhesive for affixing the supporting member to the skin surface.

5. A device according to claim 3 further comprising a protective face attached to the spacer.

6. A device according to claim 5 wherein the protective face is slidably attached to the spacer.

7. A device according to claim 1 wherein a predetermined minimum amount of force is necessary to cause the stepwise motion.

8. A device according to claim 1 wherein the stepwise motion in the direction orthogonal to the major plane of the flexible sheet is triggered by application of force in a direction orthogonal to the major plane of the sheet.

9. A device according to claim 1 wherein the stepwise motion in the direction orthogonal to the major plane of the flexible sheet is triggered by application of force in a direction parallel to the major plane of the sheet.

10. A device according to claim 9 wherein the microneedle device comprises a microneedle array.

11. A device according to claim 1 wherein the microneedle device is releasably attached to the flexible sheet.

12. A device according to claim 1 wherein the microneedle device exceeds a velocity of 4 m/s during at least a portion of the stepwise motion.

13. A device according to claim 12 wherein the microneedle device exceeds a velocity of 6 m/s during at least a portion of the stepwise motion.

14. A method of using an application device according to claim 1 for applying a microneedle array to a skin surface comprising placing the application device against the skin surface and applying a force to the application device sufficient to cause the flexible sheet of the application device to change from a convex orientation to a concave orientation with respect to the skin surface, thereby driving the microneedle array against the skin.

15. A method according to claim 14 wherein the force is applied in a direction orthogonal to the skin surface.

16. A method according to claim 14 wherein the force is applied in a direction parallel to the skin surface.

17. An application device for applying a microneedle device to a skin surface comprising a flexible sheet having a raised central area, a microneedle device attached to the raised central area, a major plane, and a periphery, wherein motion of the raised central area in a direction perpendicular to the major plane of the flexible sheet drives the microneedle device against the skin, and wherein the microneedle device comprises a microneedle array.

18. A device according to claim 17 wherein the microneedle device is releasably attached to the flexible sheet.

19. A device according to claim 17 wherein the microneedle device comprises a skin-contacting adhesive surrounding the microneedle array.

20. A method of using an application device according to claim 17 for applying the microneedle array to a skin surface comprising placing the application device against a skin surface and applying a force to the device sufficient to cause the flexible sheet of the device to change from a convex to a concave orientation with respect to the skin surface, thereby driving the microneedle array against the skin.

* * * * *